United States Patent [19]

Roubin et al.

[11] Patent Number: 5,354,257
[45] Date of Patent: Oct. 11, 1994

[54] MINIMALLY INVASIVE MEDICAL DEVICE FOR PROVIDING A RADIATION TREATMENT

[75] Inventors: Gareth S. S. Roubin, Birmingham, Ala.; Neal E. Fearnot, West Lafayette, Ind.

[73] Assignee: MED Institute, Inc., West Lafayette, Ind.

[21] Appl. No.: 647,280

[22] Filed: Jan. 29, 1991

[51] Int. Cl.$^5$ ............................................. A61M 36/12
[52] U.S. Cl. .......................................... 600/7; 600/3; 128/658
[58] Field of Search .................. 600/3, 7; 128/653.1, 128/654, 657, 659, 772; 604/164, 282; 250/496.1, 497.1

[56] References Cited

U.S. PATENT DOCUMENTS

| | | |
|---|---|---|
| 2,546,761 | 3/1951 | Loftus . |
| 4,244,357 | 1/1981 | Morrison . |
| 4,554,929 | 11/1985 | Samson et al. ................. 128/772 |
| 4,819,618 | 4/1989 | Liprie ............................... 600/3 |
| 5,001,825 | 3/1991 | Halpern ......................... 128/772 |
| 5,135,503 | 8/1992 | Abrams ......................... 604/164 |
| 5,213,561 | 5/1993 | Weinstein et al. ............... 600/7 |

FOREIGN PATENT DOCUMENTS 2348715 11/1977 France .
2203650 10/1988 United Kingdom ................ 128/772

OTHER PUBLICATIONS

"Wire Guides", *Cook Diagnostic Interventional Products for Radiology, Cardiology and Surgery*, Cook Incorporated, Bloomington, Indiana, 1986, pp. 3, 6, and 18.

*Primary Examiner*—Randall L. Green
*Assistant Examiner*—P. Zuttarelli
*Attorney, Agent, or Firm*—Richard J. Godlewski

[57] ABSTRACT

A minimally invasive intravascular medical device for providing a radiation treatment in a body passageway such as a coronary vessel of the vascular system. The device includes a flexible elongated member having distal and proximal portions. The distal portion is percutaneously insertable into a vessel and includes a distal end that is directable through the vessel to the treatment site. A radiation source is attached about the distal portion for delivering a radiation treatment to the walls a vessel having a stent positioned thereagainst. The distal portion of the elongated member includes a wire coil positioned about the tapered distal end of a mandril wire. The combination of the wire coil and the tapered distal end of the mandril wire provides variable flexibility to the distal portion of the device. The distal portion also has a predetermined curvature for directing the distal end of the device through the vessel. A safety wire is also extendable through the passageway of the wire coil to provide further flexibility to the distal portion. The radiation source is fixedly positioned about either the tapered distal end of the mandril wire or the safety wire in the passageway of the wire coil. An annular recess is included about the tapered distal end of the mandril wire to fixedly position a source of radioactive material therein.

14 Claims, 3 Drawing Sheets

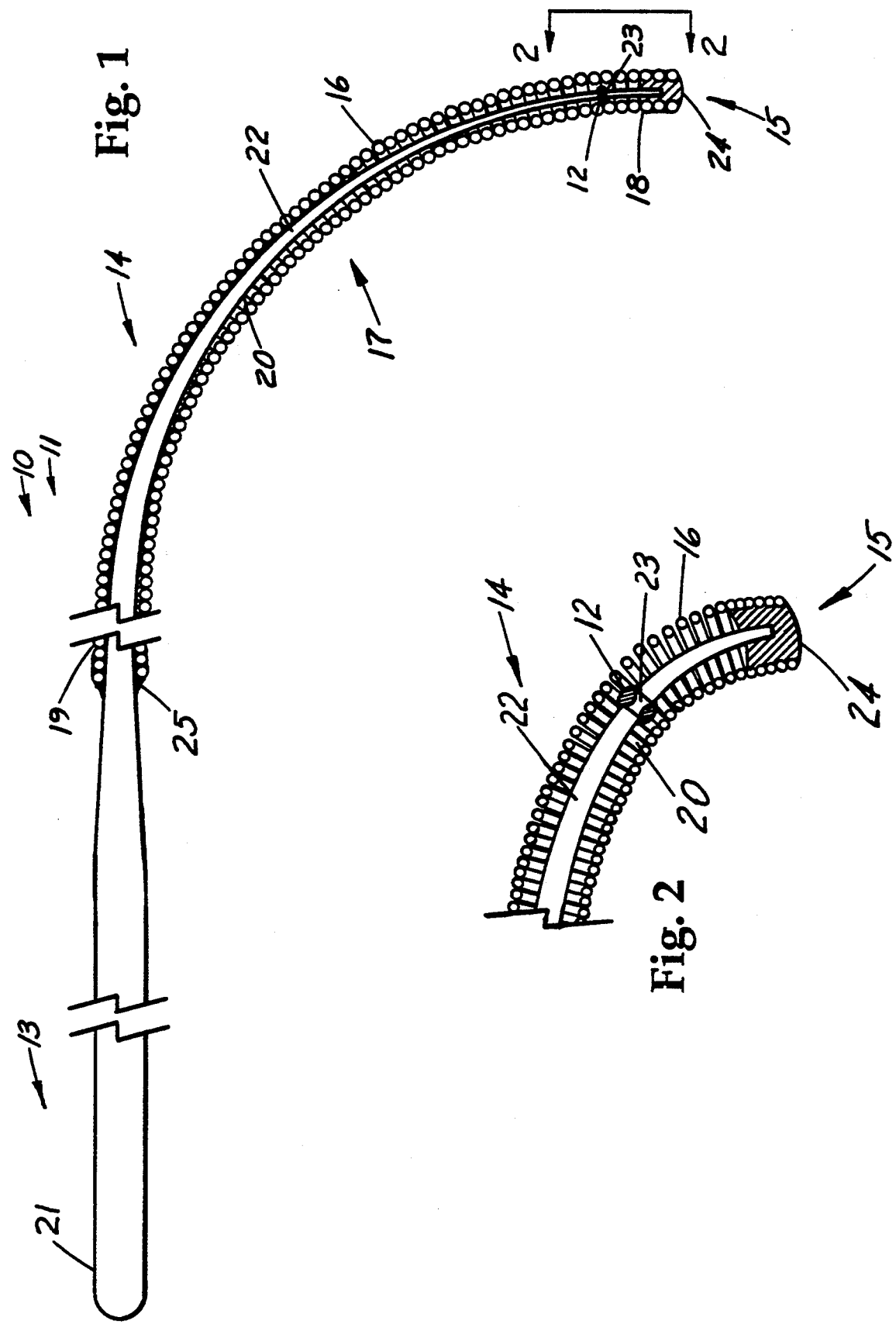

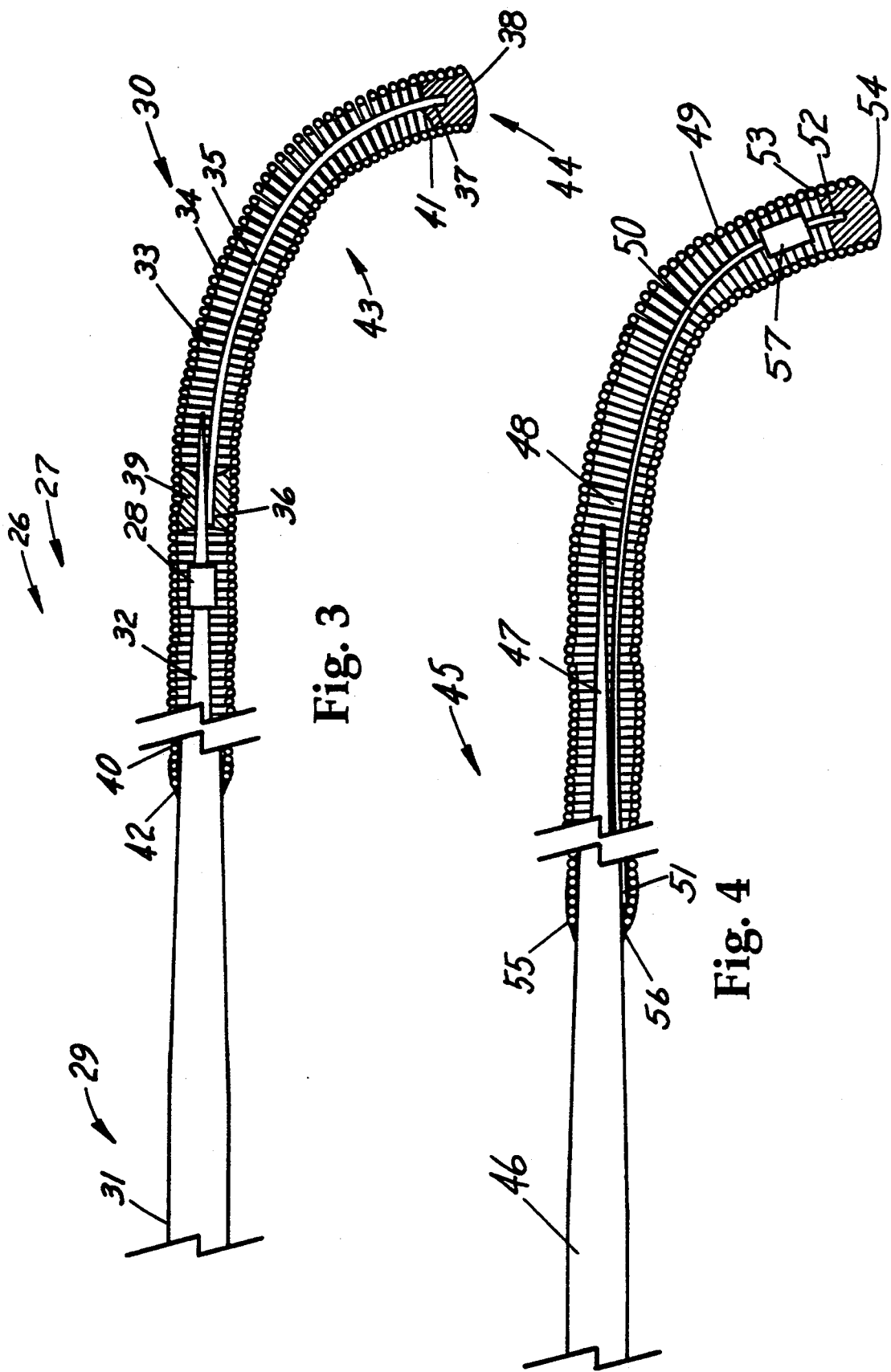

5,354,257

MINIMALLY INVASIVE MEDICAL DEVICE FOR PROVIDING A RADIATION TREATMENT

TECHNICAL FIELD

This invention relates to minimally invasive medical devices and, in particular, a minimally invasive medical device such as a wire guide or catheter for providing a radiation treatment in a body passageway or vessel.

BACKGROUND OF THE INVENTION

Occlusion of the coronary arteries can decrease blood flow to the extent that a myocardium infarction occurs. This typically occurs due to cholesterol or plaque depositing on the vessel walls and subsequently building up to occlude the vessel. As a result, several minimally invasive procedures such as balloon angioplasty or laser ablation are utilized to reopen or enlarge the lumen of the vessel. In addition, a coronary stent is positioned in the treated vessel to maintain the patency of the vessel. However, one problem is that smooth muscle proliferates or intimal hyperplasia occurs in response to the presence of the stent in the vessel. As a result, restenosis of the vessel typically occurs within a period of six months.

Another problem is that abrasion or dissection of the vessel wall may occur during the therapeutic procedure to reopen or enlarge the lumen of the vessel. As a result, thrombi formation and occlusion of the vessel lumen may also occur.

Not only are these problems associated with the coronary vessels but are applicable to other parts of the vascular system, such as the occlusion of the femoral or iliac vessels.

SUMMARY OF THE INVENTION

The foregoing problems are solved and a technical advance is achieved with an illustrative minimally invasive medical device for providing a radiation treatment in a body passageway such as a vessel in the vascular system. The localized radiation treatment in the vessel decreases reproduction of intimal and smooth muscle cells to prevent or curtail intimal hyperplasia and smooth muscle proliferation. Advantageously, restenosis of the treated vessel is significantly minimized. The illustrative minimally invasive medical device such as, for example, a wire guide or catheter, comprises a flexible elongated member having proximal and distal portions. The distal portion is insertable in a body passageway such as a coronary vessel. The distal portion also advantageously includes a distal end that is directable through the tortuous segments of the coronary vessels. The device also includes a radiation source attached about the distal portion for delivering the radiation treatment to the affected area of the vessel.

In the preferred embodiment, the distal portion of the device has a predetermined longitudinal curvature for advantageously directing the distal end through the coronary vessels. The distal portion includes a wire coil having distal and proximal ends and a passageway extending longitudinally therebetween. The elongated member comprises a cylindrical first wire having a tapered distal end which is positioned in the passageway of the coil and attached thereto. This advantageously provides the distal portion with variable flexibility for atraumatic insertion of the device.

The proximal portion of the cylindrical first wire has a uniform diameter. The outer diameter of the distal portion wire coil and the proximal portion of the first wire are within a close tolerance of each other to minimize trauma and abrasion to the vessel wall during insertion to the affected vessel site.

The tapered distal end of the first wire extends to the distal end of the wire coil and is attached thereto. The radiation source is fixedly positioned about the tapered distal end of the first wire in the passageway of the wire coil. The tapered distal end of the first wire also includes an annular recess thereabout for fixedly positioning the radiation source therein. The radiation source is positioned a predetermined distance from the distal end of the wire coil to permit controlled irradiation of the affected area.

The tapered distal end of the first wire advantageously provides variable flexibility to the distal portion of the minimally invasive device. To provide constant flexibility about the distal end of the wire coil, an enhancement to the device includes a second wire that is attached about the distal end of the wire coil. The second wire extends longitudinally in the passageway of the wire coil to the tapered distal end of the first wire, where the proximal end of the second wire is attached to the coil and the tapered distal end of the first wire. The radiation source is positioned about the tapered distal end of the first wire in the wire coil passageway.

In another enhancement, the proximal end of the second wire extends to the proximal end of the wire coil and is attached to the proximal coil end and about the tapered distal end of the first wire. The radiation source is fixedly positioned about the second wire in the passageway of the coil, preferably, a predetermined distance from the distal end thereof. For uniform irradiation of the vessel, the radiation source includes a sleeve of radioactive material positioned about either the first or second wire in the passageway of the wire coil.

In another aspect of the invention, the elongated member of the minimally invasive device comprises a tube having distal and proximal ends and a passageway extending longitudinally therebetween. The radiation source includes radioactive material which is fixedly positioned about the distal end of the tube and passageway. The tube is advantageously positioned about a wire guide inserted in the vessel for directably guiding the device to the affected area of the vessel. Advantageously, both aspects of the invention may be used as a minimally invasive intravascular device for providing selective radiation treatment to any area of the vascular system.

BRIEF DESCRIPTION OF THE DRAWING

FIG. 1 depicts the minimally invasive medical device of the present invention;

FIG. 2 depicts an enlarged view of the distal portion of the medical device of FIG. 1;

FIG. 3 depicts an alternative enhancement to the minimally invasive medical device of FIG. 1;

FIG. 4 depicts a second alternative enhancement to the minimally invasive medical device of FIG. 1;

DETAILED DESCRIPTION

Figure 5:
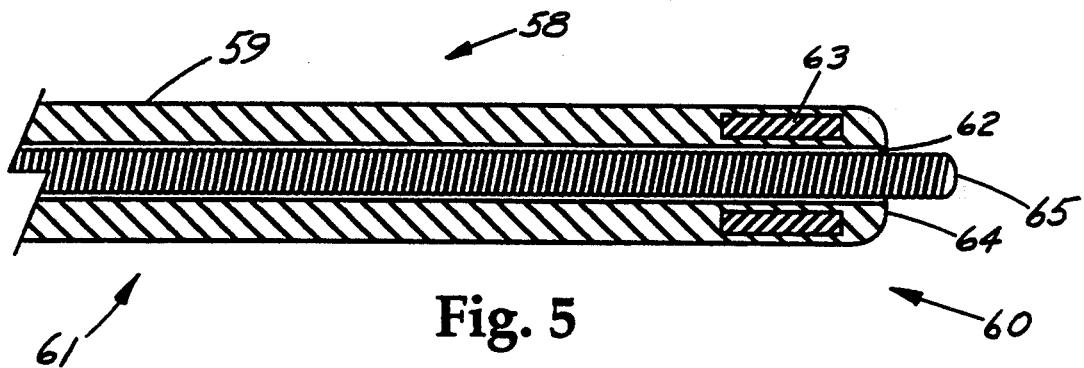
FIG. 5 depicts another aspect of the minimally invasive medical device of the present invention.

Depicted in FIG. 1 is preferred embodiment of an illustrative minimally invasive medical device 10, such as a wire guide, for providing a radiation treatment in a body passageway. This minimally invasive medical device has particular application as a percutaneously inserted intravascular device for providing a radiation treatment to the area of a coronary vessel having, for example, a stent positioned therein. Device 10 comprises flexible elongated member 11 and radiation source 12. Flexible elongated member 11 includes proximal portion 13 and distal portion 14. The distal portion is insertable in a body passageway such as a coronary artery of the vascular system and has a distal end 15 that is directable through the vascular system to the treatment site. Radiation source 12 comprises commercially available iridium radioactive material attached about distal portion 14 as shown.

Distal portion 14 includes wire coil 16 of commercially available 0.004" diameter stainless steel wire that is wound into a coil having an outside diameter of approximately 0.0183" to 0.0190" and a length of approximately 6 to 9 cm. Distal portion 14 has approximately a 90° longitudinal curvature 17 that extends for about 15 mm from distal end 15. As a result, distal end 15 is directable through the body passageway. Wire coil 16 includes distal end 18, proximal end 19, and passageway 20 extending longitudinally therebetween.

Flexible elongated member 11 comprises a stainless steel mandril wire 21 having a uniform diameter of 0.018" about the proximal portion 13. This uniform diameter is within a tolerance of −0.0015" of the wire coil diameter. Mandril wire 21 is approximately 40 cm in length and has a longitudinally tapered distal end 22 for a length of approximately 15 cm. Tapered distal end 22 of the mandril wire is inserted through passageway 20 and attached to distal coil end 18 in a well-known manner by, for example, weld 24. Proximal coil end 19 is attached to tapered distal end 22 in a well-known manner using, for example, soft solder 25. Flexible elongated member 11, known as a Cope Mandril wire guide, is commercially available from Cook Incorporated, Bloomington, Ind.

Tapered distal end 22 also includes an annular recess 23 circumferentially positioned thereabout approximately 10 mm from directable distal end 15. Radiation source 12 comprising a ring of commercially available iridium radioactive material is fixedly positioned in annular recess 23 for providing the radiation treatment. FIG. 2 depicts an enlarged view of annular recess 23 and radiation source 12 fixedly positioned therein.

Figure 7:
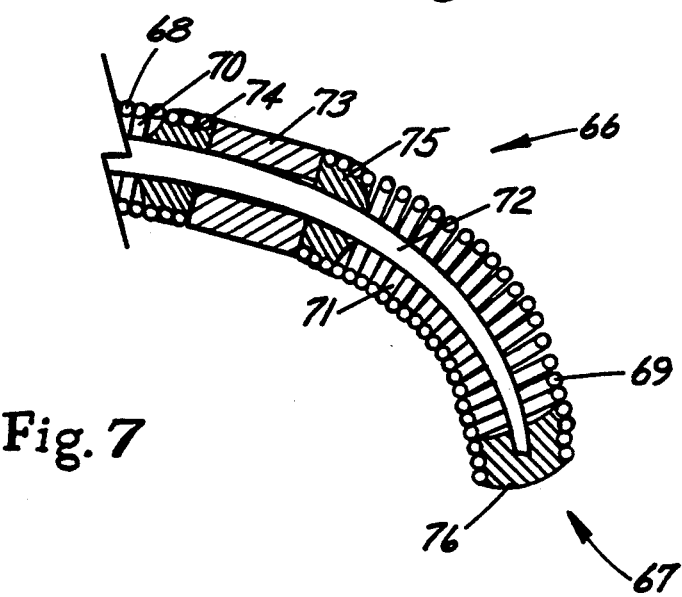
FIG. 7 depicts an enhancement to the distal portion of the medical device of FIG. 1.

Depicted in FIG. 7 is distal portion 66 of a minimally invasive medical device which includes an enhancement to the device of FIG. 1. Distal portion 66 includes proximal wire coil 68 and distal wire coil 69 having respective longitudinally extending passageways 70 and 71. The elongated flexible member of the device includes a mandril wire having tapered distal end 72. The tapered distal end of the mandril wire extends longitudinally through the wire coil passageways. The distal ends of the mandril wire and distal wire coil 69 are attached together using, for example, weld 76. This forms directable end 67 of distal portion 66 of the minimally invasive medical device. The medical device also includes radiation source 73 which is a tubular sleeve of commercially available iridium radioactive material positioned about tapered distal end 72 of a mandril wire and between proximal wire coil 68 and distal wire coil 69. Wire coils 68 and 69 are wound from commercially available 0.004" stainless steel wire into coils having an outside diameter of approximately 0.0183" to 0.0190". The tubular sleeve has an outside diameter approximating that of the wire coils. Proximal wire coil 68 is positioned over the tapered distal end of the mandril wire with the proximal end of the coil being affixed thereto with, for example, soft solder (not shown). Tubular sleeve radiation source 73 is positioned about the tapered distal end of the mandril wire next to the distal end of proximal wire coil 68. The abutting ends of the proximal wire coil and tubular sleeve are affixed to tapered distal end 72 of the mandril wire using, for example, soft solder 74. Distal wire coil 69 is positioned about the tapered distal end of the mandril wire abutting the proximal end of the tubular sleeve radiation source. The abutting ends of the distal wire coil and tubular sleeve are affixed to tapered distal end 72 of the mandril wire using, for example, soft solder 75.

Depicted in FIG. 3 is minimally invasive medical device 26 which includes an alternative enhancement to the minimally invasive device of FIG. 1. Medical device 26 includes flexible elongated member 27 and radiation source 28. The flexible elongated member includes proximal portion 29 and distal portion 30. Distal portion 30 has longitudinal curvature 43 and directable distal end 44. With this enhancement, mandril wire 31 has distal end 32 that is tapered a shorter distance of, for example, 7 cm and extends only partially through wire coil passageway 33 of wire coil 34. Wire coil 34 has proximal end 40, distal end 41, and passageway 33 extending longitudinally therebetween. The proximal end of the coil is attached to tapered distal end 32 in a well-known manner using, for example, soft solder 42. A safety second wire 35 of, for example, 0.003" by 0.008" rectangular stainless steel having proximal end 36 and distal end 37 is inserted into passageway 33 of wire coil 34. The distal ends of the safety wire and wire coil are attached in a well-known manner using, for example, weld 38. Proximal end 36 of the safety wire extends through passageway 33 to tapered distal end 32 of mandril wire 31. Tapered distal end 32 and proximal safety wire end 36 are attached to wire coil 34 in a well-known manner using, for example, soft solder 39, as shown. Flexible elongated member 27 is also commercially available from Cook Incorporated, Bloomington, Ind. Radiation source 28 comprising, for example, a sleeve of iridium radioactive material, is fixedly positioned in a well-known manner about tapered distal end 32 in wire coil passageway 33 proximal to solder joint 39.

Depicted in FIG. 4 is minimally invasive medical device 45 which is a second alternative enhancement to the device of FIG. 1. Similar to the enhancement depicted in FIG. 3, mandril wire 46 having distal end 47 is tapered a distance of, for example, 7 cm, and extends only partially into passageway 48 of wire coil 49. However, safety second wire 50 having proximal end 51 and distal end 52 extends approximately the entire length of wire coil passageway 48. Distal safety wire end 52 is attached to distal coil end 53 in a well-known manner using, for example, weld 54. Proximal safety wire end 51 and tapered distal wire end 47 are attached to proximal wire coil end 55 in a well-known manner using, for example, soft solder 56. This enhanced minimally invasive medical device is also commercially available from Cook Incorporated, Bloomington, Ind. Radiation source 57 comprising, for example, a sleeve of iridium radioactive material, is fixedly positioned about safety second wire 50 in wire coil passageway 48 a predetermined distance, for example, 5 mm from distal wire end 52.

Depicted in FIG. 5 is minimally invasive medical device 58 which forms another aspect of the present invention. Minimally invasive medical device 58, such as a catheter, comprises elongated member tube 59 having distal portion 60, proximal portion 61, and passageway 62 extending longitudinally therebetween. The device further comprises radiation source 63 attached about distal portion 60. In particular, radiation source 63 comprises a tubular sleeve of commercially available iridium radioactive material. Elongated member tube 59 is formed in a well-known manner from any of a number of commercially available plastic materials such as polyethylene, polyurethane, or polytetrafluoroethylene. Tubular sleeve radiation source 63 is fixedly positioned in the distal portion of the elongated member catheter about the passageway by embedding the sleeve a short distance such as 5 mm from distal end 64 of the tube. The device also includes wire guide 65 which is percutaneously inserted and guided into the vessel. Catheter 59 is then inserted over the wire guide and directed to the treatment site in the vessel.

Figure 6:
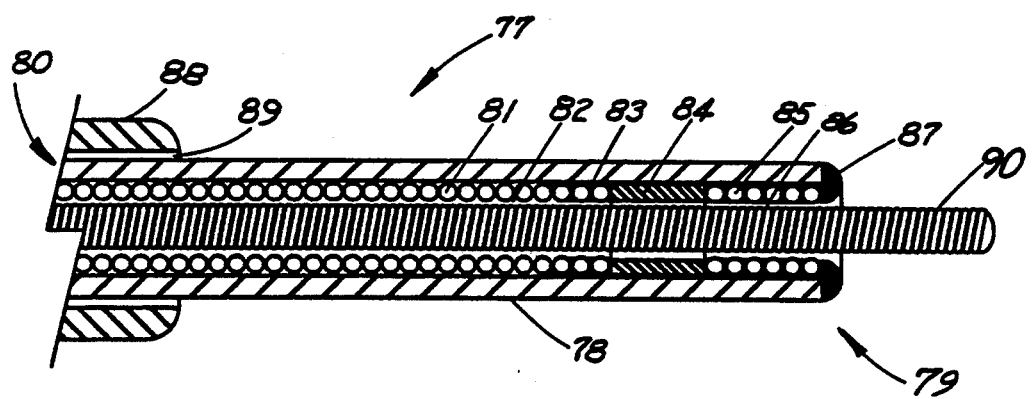
FIG. 6 depicts a second aspect of the minimally invasive medical device of the present invention.

Depicted in FIG. 6 is minimally invasive medical device 77 which forms a second aspect of the present invention. Minimally invasive medical device 77, such as a catheter, comprises elongated member tube 78 having distal portion 79, proximal portion 80, and a passageway extending longitudinally therebetween. The device further comprises radiation source 84 attached about distal portion 79 in the passageway thereof between proximal wire coil 81 and distal wire coil 85. In particular, radiation source 84 comprises a tubular sleeve of commercially available iridium radioactive material having a passageway extending longitudinally between passageways 82 and 86 of wire coils 81 and 85, respectively. The tubular sleeve radiation source is fixedly positioned about the passageway of the elongated member tube between the proximal and distal wire coils 81 and 85 in a well-known manner using, for example, commercially available adhesive to form joints 83 and 87. The adhesive extends the entire length of distal wire coil 85 to form a rounded surface at the distal end of the coil and elongated member tube. Elongated member tube 78 is formed in a well-known manner from any of a number of commercially available plastic materials. The flexible elongated member is available from Cook Incorporated, Bloomington, Ind., and is known as the Sos Interventional Wire Guide. The flexible elongated member tube has an outer diameter of approximately 0.038" which is insertable into passageway 89 of commercially available guiding catheter 88. The minimally invasive medical device also includes wire guide 90 which is percutaneously inserted and guided into the desired coronary vessel. Flexible elongated member tube 78 is then inserted over the wire guide and directed to the treatment site in the coronary vessel through the passageway of the guiding catheter.

It is to be understood that the above-described minimally invasive intravascular medical device for providing a radiation treatment in a body passageway is merely an illustrative embodiment of the principles of this invention and that other devices, instruments, or apparatus may be devised by those skilled in the art without departing from the spirit and scope of this invention. In particular, it is contemplated that many commercially available wire guides and catheters may be modified to attach a radiation source about the distal end thereof for providing a radiation treatment to a body passageway and, in particular, preventing intimal hyperplasia and smooth muscle proliferation which causes stenosis or restenosis of the passageway. Although described as being particularly applicable to the vascular system using well-known percutaneous insertion techniques, it is contemplated that the minimally invasive device is applicable for providing treatment to the pulmonary system as well as the gastrointestinal tract. Treatment of the biliary and urinary system are also contemplated with wire guides and catheters, particularly adapted with the radiation source for treating the particular anatomical system.

What is claimed is:

1. A minimally invasive intravascular medical device for providing a radiation treatment, comprising:
   a cylindrical first wire having a first uniform outer diameter and a longitudinally tapered distal end;
   a wire coil including a distal end, a proximal end, and a passageway extending longitudinally therebetween, said tapered distal end of said first wire extending longitudinally in said passageway of said wire coil, said proximal end of said wire coil being attached to said first wire, said coil having a second outer diameter within a predetermined tolerance of said first uniform outer diameter, said wire coil having a predetermined longitudinal curvature;
   a second wire having a distal end attached to said wire coil and a proximal end and extending longitudinally in said passageway to said tapered distal end of said first wire, said proximal end of said second wire being attached to said wire coil and said first wire in said longitudinal passageway; and
   a sleeve of radioactive material fixedly positioned at least partially around said second wire in said passageway a predetermined distance from said distal end of said wire coil.

2. A minimally invasive medical device for providing a radiation treatment in a body passageway, comprising:
   a flexible elongated member tube having a proximal portion, a distal portion, and a hollow passageway extending longitudinally therethrough, said distal portion being insertable in said body passageway over a guide positioned therein and having a distal end directable through said body passageway over the guide; and
   a radiation source fixedly positioned and embedded in said tube around said hollow passageway of said tube.

3. The device of claim 2 further comprising a wire guide slidable through said hollow passageway of said tube.

4. A minimally invasive medical device for providing a radiation treatment in a body passageway, comprising:
   a flexible elongated member having a proximal portion, a distal portion, and a first wire having a tapered distal end extending longitudinally in said distal portion, said distal portion being insertable in said body passageway and having a predetermined longitudinal curvature and a distal end directable through said body passageway, said distal portion also including a wire coil having a distal end, a proximal end, and a passageway extending longitudinally therebetween, said tapered distal end of said first wire extending longitudinally in said passageway of said wire coil and being attached to said wire coil; and a radiation source attached at least partially around said tapered distal end of said first wire.

5. The device of claim 4 wherein said tapered distal end of said first wire includes an annular recess and said radiation source is fixedly positioned in said annular recess.

6. The device of claim 4 wherein said distal portion includes a second wire having a proximal end attached to said wire coil and to said first wire and a distal end attached to said wire coil and extending longitudinally in said passageway of said wire coil.

7. The device of claim 6 wherein said proximal end of said second wire extends and is attached to said proximal end of said wire coil.

8. The device of claim 7 wherein said wire coil has a first predetermined outer diameter and wherein a proximal portion of said first wire has a second predetermined outer diameter within a predetermined tolerance of said first outer diameter.

9. A minimally invasive intravascular medical device for providing a radiation treatment, comprising:

a first wire having a longitudinally tapered distal end;

a wire coil positioned around said tapered distal end of and attached to said first wire and having a distal end, a proximal end, and a passageway extending longitudinally therebetween; and a radiation source attached at least partially around said first wire in said passageway of said wire coil.

10. The device of claim 9 wherein said wire coil has a predetermined longitudinal curvature.

11. The device of claim 10 wherein said radiation source includes radioactive material fixedly positioned at least partially around said tapered distal end of said first wire in said passageway.

12. The device of claim 10 wherein said tapered distal end of said first wire includes an annular recess and wherein said radiation source includes radioactive material fixedly positioned in said annular recess.

13. The device of claim 10 further comprising a second wire attached to said wire coil and extending longitudinally in said passageway to said first wire.

14. The device of claim 13 wherein said radiation source includes radioactive material fixedly positioned at least partially around said second wire in said passageway a predetermined distance from said distal end of said wire coil.

* * * * *